(12) United States Patent
Santus et al.

(10) Patent No.: US 7,267,827 B2
(45) Date of Patent: Sep. 11, 2007

(54) THERAPEUTIC COMPOSITIONS FOR INTRANASAL ADMINISTRATION WHICH INCLUDE KETOROLAC

(75) Inventors: Giancarlo Santus, Milan (IT); Giuseppe Bottoni, Bergamo (IT); Ettore Bilato, Padova (IT)

(73) Assignee: Recordati S.A., Chiasso (CH)

( * ) Notice: Subject to any disclaimer, the term of this patent is extended or adjusted under 35 U.S.C. 154(b) by 1225 days.

(21) Appl. No.: 09/903,665

(22) Filed: Jul. 13, 2001

(65) Prior Publication Data

US 2002/0077346 A1 Jun. 20, 2002

Related U.S. Application Data

(63) Continuation of application No. 08/383,707, filed on Feb. 1, 1995, now Pat. No. 6,333,044, which is a continuation of application No. 07/875,700, filed on Apr. 29, 1992, now abandoned.

(30) Foreign Application Priority Data

Jul. 22, 1991 (IT) ............................... MI91A2024

(51) Int. Cl.
*A61K 9/00* (2006.01)
*A61K 31/40* (2006.01)

(52) U.S. Cl. ..................... 424/434; 514/413; 514/947

(58) Field of Classification Search ............... 424/434, 424/43, DIG. 15; 514/300, 413, 947, 91, 514/183, 359, 408, 638, 887, 937, 944, 946
See application file for complete search history.

(56) References Cited

U.S. PATENT DOCUMENTS

| | | | |
|---|---|---|---|
| 4,089,569 A | 5/1978 | Muchowski ............... 514/416 |
| 4,089,969 A * | 5/1978 | Muchowski et al. ........ 514/416 |
| 4,478,822 A | 10/1984 | Haslam .................... 424/78 |
| 4,778,810 A | 10/1988 | Wenig et al. .............. 514/263 |
| 4,885,287 A | 12/1989 | Hussain ................... 514/159 |
| 4,919,939 A | 4/1990 | Baker | |
| 4,943,587 A * | 7/1990 | Cetenko et al. .......... 514/233.2 |
| 4,973,596 A | 11/1990 | Cohen ...................... 514/354 |
| 4,994,439 A | 2/1991 | Longenecker et al. | |
| 5,049,386 A | 9/1991 | Eppstein et al. | |
| 5,091,182 A | 2/1992 | Ong et al. | |
| 5,122,127 A * | 6/1992 | Stanley ..................... 604/890.1 |
| 5,143,731 A | 9/1992 | Viegas et al. | |
| 5,855,907 A | 1/1999 | Peyman | |
| 6,090,368 A | 7/2000 | Zia et al. ...................... 424/45 |

FOREIGN PATENT DOCUMENTS

| | | | |
|---|---|---|---|
| JP | 03-072433 | * | 3/1991 |
| WO | WO88/004929 | | 7/1988 |
| WO | WO-90/001322 | | 2/1990 |
| WO | WO90/07333 | | 7/1990 |

OTHER PUBLICATIONS

JP 03-072433, Foamy Aerosol Preparation, Patent Abstracts of Japan, Mar. 27, 1991, abstract.*
Rubin, M.D. et al Comparison Long-Term Safety of Ketorolac Tromethamine and Aspirin in the Treatment of Chronic Pain. Pharmacotherapy (1990) 10(6pt. 2) pp.106S-110S.
Santus et al., Nasal Formulations of Ketoroloac Tromethamine Technological Evaluation-Bioavailability and Tolerability in Rabbits, IL Farmaco, 48 (12), 1709-1723; 1993.
Mroszczak, E. J., et al., Ketorolac Tromethamine Absorption, Distribution, Metabolism, Excretion, and Pharmacokinetics in Animals and Humans, Drug Metab. Dispos., 15 (5):618-626, 1987.
Chien, Y.W. and Chang, S.F., Historical Development of Transnasal Systemic Medications; In: *Transnasal Systemic Medications*, edited by Y.W. Chien, Elsevier Science Publishers B.V., Amsterdam, 1985.
Buckley, M.M.T., *Drugs* 39:86-109, 1990.
Yu, D., *Pharmaceutical Research 5* :457-462, 1988.
Rooks, W.H. *Drugs Exptl. Clin. Res.* 11:479-492, 1985.
O'Hara, D.A., *Clin. Pharmacol. Ther.* 41:556-561, 1987.
Illum, L., *International Journal of Pharmaceutics 39*:189-199, 1987.
Morimoto, K., *J. Pharm. Pharmacol.* 37:134-136, 1985.
Hirai, S., *International Journal of Pharmaceutics 9*:165-172, 1981.
Pennington, A.K., *International Journal of Pharmaceutics 43*:221-224, 1988.
DePonti, R., *Drug Development and Industrial Pharmacy 17*:1419-1436, 1991.

* cited by examiner

Primary Examiner—Frederick Krass
(74) Attorney, Agent, or Firm—Darby & Darby

(57) ABSTRACT

An analgesic/anti-inflammatory pharmaceutical dosage form which comprises an effective amount of an active ingredient selected from the group consisting of racemic 5-benzoyl-2,3-dihydro-1H-pyrrolizine-1-carboxylic acid, optically active forms thereof and pharmaceutically acceptable salts thereof, in combination with a pharmaceutically acceptable excipient or diluent, said dosage form being an intranasally administrable dosage form.

12 Claims, No Drawings

THERAPEUTIC COMPOSITIONS FOR INTRANASAL ADMINISTRATION WHICH INCLUDE KETOROLAC

This application is a continuation of U.S. patent application Ser. No. 08/383,707, filed on Feb. 1, 1995, now U.S. Pat. No. 6,333,044, which in turn is a continuation of U.S. patent application Ser. No. 07/875,700, filed on Apr. 29, 1992, now abandoned, which claims priority under 35 U.S.C. §119 to Italian patent application Serial No. MI 91 A 002024 filed on Jul. 22, 1991.

FIELD OF THE INVENTION

This invention relates to therapeutic compositions with analgesic and anti-inflammatory activity, suitable for intranasal administration, which include KETOROLAC® or its pharmaceutically acceptable salts as the active ingredient.

This invention also relates to a therapeutic method which provides for the administration of KETOROLAC® or its salts by the intranasal route.

BACKGROUND OF THE INVENTION

KETOROLAC® or 5-benzoyl-2,3-dihydro-1H-pyrrolizine-1-carboxylic acid, the formula of which is:

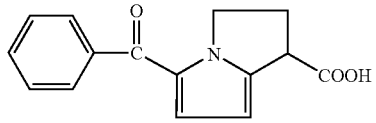

has been known for several years (U.S. Pat. No. 4,089,969) and is used in human therapy as an analgesic and an anti-inflammatory.

Both the racemic form and each of the dextro and levo isomers of this compound are known. Many pharmaceutically acceptable salts, the most commonly used of which is the tromethamine (2-amino-2-hydroxymethyl-1,3-propanediol) salt, are also known. Hereinafter, the name KETOROLAC® shall encompass individually or collectively the racemic mixture or either optically active compound and shall encompass the free acid as well as the tromethamine salt or any other pharmaceutically acceptable salt of any one of the foregoing.

Ample literature is available on KETOROLAC® (for instance, "KETOROLAC®—A review of its pharmacodynamic and pharmacokinetic properties and its therapeutic potential", *Drugs* 39(1): 86-109, 1990. It is described as a drug with considerably higher analgesic and anti-inflammatory activity than many other non-steroid anti-inflammatory drugs. Most significantly, it has higher analgesic activity than morphine, without the well-known side effects of the latter.

In the several pharmacological and clinical trials involving KETOROLAC® that have been conducted, this drug was administered both by the oral route and by injection (in turn, both intravenous and intramuscular). Regardless of the administration route, KETOROLAC® proved active and was found comparatively more active than the better known non-steroid drugs with analgesic and anti-inflammatory activity. However, about 10% of the patients treated (20 doses of 30 mg each administered over five days) by the intramuscular route suffered from one or more undesirable side effects such as somnolence, local (injection site) pain, sweating, nausea, headache, dizziness, vomiting, pruritus, and vasodilation.

The incidence of side effects was even higher (around 32%) in the patients treated with KETOROLAC® by the oral route for a few days. In the case of oral administration, gastrointestinal disorders (nausea, g.i. pain, dyspepsia, diarrhea, flatulence, g.i. fullness, vomiting) were noted in up to 50% of the patients in addition to side effects incident to i.m. administration.

Intravenous administration is inconvenient and is limited to the treatment of acute conditions.

On the whole, the data available to date clearly describe a drug which is very active, but still unsatisfactory from the point of view of convenience of administration and/or side effects.

SUMMARY OF THE INVENTION

We have now found that it is possible to prepare analgesic/anti-inflammatory formulations containing KETOROLAC® as an active ingredient, which are suitable for intranasal administration and that KETOROLAC® so administered is rapidly and thoroughly absorbed, giving therapeutic effects equivalent to those obtained by the intravenous route (acute treatments) or the intramuscular or oral routes (extended or chronic treatments), without inducing severe side effects. Most important, any possibility of gastrointestinal disorders is excluded, while disorders caused by CNS stimulation are considerably reduced both in incidence (e.g. number of patients affected) and intensity.

Another aspect of the present invention is directed to a therapeutic method for the treatment of inflammatory processes and for the therapy of pain of a traumatic or pathologic origin, which method comprises administering by the intranasal route an analgesic/anti-inflammatory amount of KETOROLAC® along with an absorption promoter and pharmaceutically acceptable diluents and/or excipients.

The new method provides for the intranasal administration of KETOROLAC® doses ranging between 0.5 and 40 mg, preferably between 5 and 30 mg, and is particularly effective in acute therapies, where a very rapid systemic delivery is required especially one not accompanied by the drawbacks of i.v. delivery (hospitalization, cost, etc.).

DETAILED DESCRIPTION OF THE INVENTION

All cited patents and literature are incorporated by reference in their entirety.

Although nasal administration to mammals (especially humans) of certain therapeutic agents is known, it is not to be presumed that all therapeutic agents can be effectively administered by this route. To the contrary, many therapeutic agents cannot be nasally administered. At present, the molecules which have proved suitable for this route of administration are still very few and consist essentially of only small peptide or hormone molecules (such as calcitonin, cerulean, β-endorphin, glucagon, horseradish peroxidase, B-interferon, oxytocin and insulin) in special formulations. The ability of drug molecules to be absorbed by the nasal mucous membranes is utterly unpredictable, as is the ability of intranasal formulations to avoid irritation of the mucous nasal membranes. In fact, mucous membrane irritation caused by the drug and/or excipient is the most common reason for which intranasal administration has not gained wider acceptance.

The new compositions according to the invention include the active ingredient in quantities ranging from 0.5 to 40 mg per dose, preferably 5 to 30 mg per dose, diluted in excipients such as humectants, isotoning agents, antioxidants, buffers and preservatives. A calcium chelating agent is also preferably included.

The intranasal formulations of the invention contain KETOROLAC® concentrations ranging from 5 to 20%, preferably about 15% weight/volume. Of course, the selection of the particular excipients depends on the desired formulation dosage form, i.e. on whether a solution to be used in drops or as a spray (aerosol) is desired or a suspension, ointment or gel to be applied in the nasal cavity are desired. In any case, the invention make it possible to have single-dose dosage forms, which ensure application of an optimum quantity of drug.

Administration of the present intranasal formulations provides very good absolute bioavailability of KETOROLAC, as demonstrated in tests involving rabbits. The predictive value of the rabbit model with respect to bioavailability of nasally administered KETOROLAC® in humans is art-recognized (Mroszczak, E. J. et al., *Drug Metab. Dispos.*, 15:618-626, 1987, especially Tables 1 and 3). According to the results of the rabbit tests set forth below it is extrapolated that in humans intranasal administration of a composition according to the invention in amounts ranging between 0.5 mg/kg/day and 4 mg/kg/day will generate plasma levels of KETOROLAC® within the range of 0.3-5 mg/liter of plasma.

Suitable vehicles for the formulations according to the invention include aqueous solutions containing an appropriate isotoning agent selected among those commonly used in pharmaceutics. Substances used for this purpose are, for instance, sodium chloride and glucose. The quantity of isotoning agent should impart to the vehicle (taking into account the osmotic effect of the active ingredient), an osmotic pressure similar to that of biological fluids, i.e. generally from about 150 to about 850 milliOsmoles (mOsm) preferably from about 270 to about 330 mOsm.

However, it is known that nasal mucous membranes are also capable of tolerating slightly hypertonic solutions. Should a suspension or gel be desired instead of a solution, appropriate oily or gel vehicles may be used or one or more polymeric materials may be included, which desirably should be capable of conferring bioadhesive characteristics to the vehicle.

Several polymers are used in pharmaceutics for the preparation of a gel; the following can be mentioned as nonlimiting examples: hydroxypropyl cellulose (KLUCEL®), hydroxypropyl methyl cellulose (METHOCEL®), hydroxyethyl cellulose (NATROSOL®), sodium carboxymethyl cellulose (BLANOSE®), acrylic polymers (CARBOPOL®, POLYCARBOPHIL®), gum xanthan, gum tragacanth, alginates and agar-agar.

Some of them, such as sodium carboxymethyl cellulose and acrylic polymers, have marked bioadhesive properties and are preferred if bioadhesiveness is desired.

Other formulations suitable for intranasal administration of KETOROLAC® can be obtained by adding to the aqueous vehicle polymers capable of changing the rheologic behavior of the composition in relation to the temperature. These polymers make it possible to obtain low viscosity solutions at room temperature, which can be applied for instance by nasal spray and which increase in viscosity at body temperature, yielding a viscous fluid which ensures a better and longer contact with the nasal mucous membrane. Polymers of this class include without limitation polyoxyethylene-polyoxypropylene block copolymers (POLOXAMER®).

In addition to aqueous, oil or gel vehicles, other vehicles which may be used in the compositions according to the invention comprise solvent systems containing ethyl alcohol, isopropyl alcohol, propylene glycol, polyethylene glycol, mixtures thereof or mixtures of one or more of the foregoing with water.

In any case, a pharmaceutically acceptable buffer should be present in order to create optimum pH conditions for both product stability and tolerance (pH range about 4 to about 8; preferably about 5.5 to 7.5). Suitable buffers include without limitation tris (tromethamine) buffer, phosphate buffer, etc.

Other excipients include chemical enhancers such as absorption promoters. These include chelating agents, fatty acids, bile acid salts and other surfactants, fusidic acid, lysophosphatides, cyclic peptide antibiotics, preservatives, carboxylic acids (ascorbic acid, amino acids), glycyrrhetinic acid, o-acylcarnitine. Preferred promoters are diisopropyladipate, POE(9) lauryl alcohol, sodium glycocholate and lysophosphatidyl-choline which proved to be particularly active. Finally, the new compositions according to the invention preferably contain preservatives which ensure the microbiological stability of the active ingredient. Suitable preservatives include without limitation, methyl paraoxybenzoate, propyl paraoxybenzoate, sodium benzoate, benzyl alcohol, benzalkonium chloride and chlorobutanol.

The liquid KETOROLAC® formulations, preferably in the form of solutions, may be administered in the form of drops or spray, using atomizers equipped with a mechanical valve and possibly including a propellant of a type commercially available, such as butane, $N_2$, Ar, $CO_2$, nitrous oxide, propane, dimethyl ether, chlorofluorocarbons (e.g. FREON) etc. Vehicles suitable for spray administration are water, alcohol, glycol and propylene glycol, used alone or in a mixture of two or more.

Generally, illustrative formulations will contain the following ingredients and amounts (weight/volume):

| Ingredient | Broad Range (%) | Preferred Range (%) |
|---|---|---|
| $Na_2$ EDTA | 0.001–1 | 0.05–0.1 |
| Nipagin | 0.01–2 | 0.05–0.25 |
| POE(9) Lauryl alcohol | 0.1–10 | 1–10 |
| NaCMC (Blanose 7m8 sfd) | 0.1–5 | 0.3–3 |
| Carbopol 940 | 0.05–2 | 0.1–1.5 |
| Glycerol | 1–99 | |
| Sodium glycocholate | 0.05–5 | 0.1–1 |

It will be appreciated by those of ordinary skill that ingredients such as sodium carboxymethyl cellulose and Carbopol exist in many types differing in viscosity. Their amounts are to be adjusted accordingly. Different adjustments to each formulation may also be necessary including omission of some optional ingredients and addition of others. It is thus not possible to give an all-encompassing amount range for each ingredient, but the optimization of each preparation according to the invention is within the skill of the art.

Another, although not preferred, alternative for the intranasal administration of the KETOROLAC®-based compositions comprises a suspension of finely micronized active ingredient (generally from 1 to 200 micrometers, preferably from 5 to 100 micrometers) in a propellant or in an oily vehicle or in another vehicle in which the drug is not soluble.

The vehicle is mixed or emulsified with the propellant. Vehicles suitable for this alternative are, for instance, vegetable and mineral oils and triglyceride mixtures. Appropriate surfactants, suspending agents and diluents suitable for use in pharmaceutics are added to these vehicles. Surfactants include without limitation sorbitan sesquioleate, sorbitan monooleate, sorbitan trioleate (amount: between about 0.25 and about 1%); suspending agents include without limitation isopropylmyristate (amount: between about 0.5 and about 1%) and colloidal silica (amount: between about 0.1 and about 0.5%); and diluents include without limitation zinc stearate (about 0.6 to about 1%).

The following examples of formulations for the intranasal administration of KETOROLAC® serve to illustrate the invention without limiting its scope.

EXAMPLE 1

| Composition | % | For 10 liters |
| --- | --- | --- |
| KETOROLAC ® tromethamine | 5 | 500 g |
| EDTA disodium (chelating agent) | 0.01 | 1 g |
| NIPAGIN (preservative) | 0.1 | 10 g |
| Purified water, q.s. to | 100 | 10 L |

Method of Preparation

In a suitable vessel equipped with mixer and heating sleeve, introduce about 9 liters of purified water and heat to a temperature of 80° C.

Dissolve NIPAGIN and EDTA disodium.

Stir the solution constantly to complete dissolution of the components.

Cool the obtained solution to room temperature.

Dissolve KETOROLAC® tromethamine by stirring.

Bring to volume with water.

The isotonicity of this composition was 190 mOsm but can be adjusted e.g. to 270 mOsm by the addition of 0.3% NaCl or 2.03% of glucose.

EXAMPLE 2

| Composition | % | For 10 liters |
| --- | --- | --- |
| KETOROLAC ® tromethamine | 5 | 500 g |
| POE (9) lauryl alcohol (enhancer/promoter) | 5 | 500 g |
| NIPAGIN | 0.1 | 10 g |
| EDTA disodium | 0.01 | 1 g |
| Purified water, q.s. to | 100 | 10 L |

Method of Preparation

In a suitable vessel equipped with mixer and heating sleeve, introduce about 9 liters of purified water and heat to a temperature of 80° C.

Dissolve NIPAGIN and EDTA disodium.

Stir the solution constantly to complete dissolution of the components.

Cool the obtained solution to room temperature.

Add POE (9) lauryl alcohol and stir to complete dissolution.

Dissolve KETOROLAC® tromethamine by stirring.

Bring to volume with water.

EXAMPLE 3

| Composition | % | For 10 liters |
| --- | --- | --- |
| KETOROLAC ® tromethamine | 5 | 500 g |
| Sodium carboxymethyl cellulose | 1 | 100 g |
| Tromethamine, q.s. to pH = 6 | | |
| NIPAGIN | 0.1 | 10 g |
| Purified water, q.s. to | 100 | 10 L |

Method of Preparation

In a suitable vessel equipped with mixer and heating sleeve, introduce about 9 liters purified water and heat to a temperature of 80° C.

Dissolve NIPAGIN.

Cool the obtained solution to room temperature.

Dissolve KETOROLAC® and continue stirring to complete dissolution of the drug.

Disperse sodium carboxymethyl cellulose in the solution stirring vigorously.

Continue stirring to complete hydration of the polymer.

Adjust the pH to the required value by suitably adding tromethamine dissolved in water.

Bring to volume with water.

EXAMPLE 4

| Composition | % | For 10 liters |
| --- | --- | --- |
| KETOROLAC ® tromethamine | 5 | 500 g |
| NIPAGIN | 0.1 | 10 g |
| EDTA disodium | 0.01 | 1 g |
| CARBOPOL 940 | 0.1 | 10 g |
| Tromethamine, q.s. to pH = 7–7.4 | | |
| Glycerol | 2 | 200 g |
| Purified water, q.s. to | 100 | 10 L |

Method of Preparation

In a suitable vessel equipped with mixer and heating sleeve, introduce about 4 liters of purified water and heat to a temperature of 80° C.

Dissolve NIPAGIN and EDTA.

Cool the solution to room temperature.

Dissolve KETOROLAC® tromethamine.

Complete the dissolution of the active ingredient and adjust the pH to a value of 7.1-7.4 by adding a 5% tromethamine solution.

In a separate vessel equipped with mixer, introduce the quantity of glycerol called for in the formulation.

Introduce CARBOPOL and mix until a homogeneous dispersion in the glycerol is obtained.

Add 4 liters of purified water with vigorous stirring and continue stirring the solution to complete hydration of the polymer.

Combine the solution containing the active ingredient and the polymer solution with stirring.

If necessary, adjust the pH to the required value with the tromethamine solution.

Bring to volume with water.

EXAMPLE 5

| Composition | % | For 10 liters |
|---|---|---|
| KETOROLAC ® tromethamine | 5 | 500 g |
| LUTROL F127 | 17 | 1.7 Kg |
| EDTA disodium | 0.01 | 1 g |
| NIPAGIN | 0.1 | 10 g |
| Purified water, q.s. to | 100 | 10 L |

Method of Preparation

In a suitable vessel equipped with mixer and heating sleeve, introduce about 4 liters of purified water and heat to a temperature of 80° C.

Dissolve NIPAGIN and EDTA disodium.

Cool the solution to 4° C. and then, maintaining it between 4 and 6° C. throughout the operation, gradually add Lutrol F127 with stirring.

Continue stirring to complete hydration of the polymer.
Bring the solution to room temperature.
Dissolve KETOROLAC® tromethamine.
Bring to volume with water.

EXAMPLE 6

| Composition | % | For 10 liters |
|---|---|---|
| KETOROLAC ® tromethamine | 5 | 500 g |
| Sodium carboxymethyl cellulose | 2 | 200 g |
| EDTA disodium | 0.01 | 1 g |
| NIPAGIN | 0.1 | 10 g |
| Purified water, q.s. to | 100 | 10 L |

The procedure of Example 3 was used to make the above formulation except that no buffer was added.

EXAMPLE 7

| Composition | % | For 10 liters |
|---|---|---|
| KETOROLAC ® tromethamine | 5 | 500 g |
| LUTROL F127 | 15 | 1500 g |
| EDTA disodium | 0.01 | 1 g |
| NIPAGIN | 0.1 | 10 g |
| Purified Water, q.s. to | 100 | 10 L |

The procedure of Example 5 was used to make the above formulation.

EXAMPLE 8

| Composition | % | For 10 liters |
|---|---|---|
| KETOROLAC ® tromethamine | 5 | 500 g |
| EDTA disodium | 0.01 | 1 g |
| NIPAGIN | 0.1 | 10 g |
| Sodium glycocholate | 0.3 | 30 g |
| Purified water, q.s. to | 100 | 10 L |

The procedure of Example 1 was used except that sodium glycocholate was dissolved with the nipagin and disodium EDTA at 80° C. in water. The isotonicity of this composition was 190 mOsm; it can be adjusted e.g. to 330 mOsm by the addition of 0.44% NaCl or 3.05% glucose.

EXAMPLE 9

| Composition | % | For 10 liters |
|---|---|---|
| KETOROLAC ® tromethamine | 5 | 500 g |
| Lutrol F127 | 15 | 1500 g |
| Sodium glycocholate | 0.3 | 30 g |
| EDTA disodium | 0.01 | 1 g |
| NIPAGIN | 0.1 | 10 g |
| Purified water, q.s. to | 100 | 10 L |

The procedure of Example 5 was used except that sodium glycocholate was dissolved along with nipagin and disodium EDTA at 80° C.

EXAMPLE 10

We studied the stability of the preparations described in the Examples 1, 2, 6, 7, 8 and 9. The storing conditions were 4° C., 22° C., 45° C. and 55° C. We analyzed the preparations at the beginning of the storing period and after 1, 2, 3 and 6 months. We used UV and HPLC analysis.

The parameters tested were:

content of active compound (UV and HPLC)

content of keto and hydroxy degradation products (UV and HPLC)

appearance and color (visual examination)

pH (digital pH meter)

The results are summarized in Table 1.

TABLE 1

| Example | Temp. ° C. | Months | KTM (mg/ml) | Keto % | Hydroxy % | Appearance of solution | pH |
|---|---|---|---|---|---|---|---|
| 1 | 22 | 0 | 50.1 | 0.8 | 0.3 | light yellow | 6.2 |
|   | 45 | 2 | 50.8 | 0.2 | 0.0 | yellow | 6.5 |
|   | 45 | 3 | 49.6 | 0.2 | 0.0 | opalescent yellow | 6.5 |
|   | 45 | 6 | 51.4 | 0.4 | 0.0 | yellow with deposit | 6.5 |
| 2 | 22 | 0 | 49.0 | 0.1 | 0.3 | light yellow | 6.4 |
|   | 45 | 2 | 47.7 | 0.4 | 0.0 | yellow | 6.8 |
|   | 45 | 3 | 46.7 | 0.2 | 0.0 | yellow | 6.9 |
|   | 45 | 6 | 47.3 | 1.0 | 0.0 | yellow | 7.0 |
| 6 | 22 | 0 | 49.6 | 0.1 | 0.4 | yellow | 6.0 |
|   | 45 | 1 | 47.0 | 0.1 | 0.1 | yellow | 6.5 |
|   | 45 | 3 | 48.8 | 0.2 | 0.0 | yellow | 6.5 |
|   | 45 | 6 | 50.1 | 0.9 | 0.0 | yellow with deposit | 5.5 |
| 7 | 22 | 0 | 48.5 | 0.0 | 0.5 | light yellow | 6.7 |
|   | 55 | 1 | 49.0 | 0.8 | 0.0 | yellow gel | 6.8 |
|   | 55 | 3 | 47.1 | 1.4 | 1.9 | orange gel | 6.6 |
| 8 | 22 | 0 | 52.3 | 0.0 | 0.0 | light yellow | 6.2 |
|   | 45 | 1 | 53.2 | 0.0 | 0.0 | yellow | 6.4 |
|   | 45 | 3 | 54.3 | 0.5 | 0.0 | yellow | 6.5 |
| 9 | 22 | 0 | 48.7 | 0.0 | 0.0 | light yellow | 6.7 |
|   | 45 | 1 | 51.7 | 0.0 | 0.0 | yellow | 6.8 |

EXAMPLE 11

We tested in vitro the thermosetting properties of some preparations (Examples 1, 2, 7, 9). We sprayed a standardized amount of every preparation to a 37° C. constant-temperature, vertical glass surface and we measured the time that the drops of preparation spent to cover 10 cm. The speed of solution in moving on the constant-temperature surface is an indicator of the thermosetting properties of the dosage form. Examples 7 and 9 gave the best results in terms of thermosetting properties.

The results are reported in Table 2.

TABLE 2

| Preparation | Time to Cover 10 cm |
|---|---|
| $H_2O$ | 3 sec. |
| Example 1 | 3 sec. |
| Example 2 | 3 sec. |
| Example 7 | 12 sec. |
| Example 9 | 15 sec. |

EXAMPLE 12

We studied the nasal absorption and the local tolerance of four preparations (Examples 1, 6, 8, 9) in White New Zealand rabbits (three rabbits for each experimental group plus three controls). Each rabbit received a active preparation in one nostril and its placebo in the other. Each animal received 2 mg/kg of KETOROLAC® tromethamine (KTM), twice a day for seven days and once on the eighth day. The control rabbits were treated, after seven days of nasal administration of physiologic solution, with 2 mg/kg of KTM by intravenous route once. After the last treatment plasma samples were collected at several times and KTM plasma levels were investigated by HPLC. After the last blood sample was drawn all the animals were killed by excision of femoral arteries, after having been completely anaesthetized. Nasal turbinates, larynx and pharynx were removed and subjected to histological examinations.

Pharmacokinetic parameters are reported in Tables 3, 4, 5, 6, 7 and in FIG. 1. The local (nasal mucous) tolerance data showed good tolerance of the KETOROLAC-containing intranasal preparations with the formulation of Example 1 being the best tolerated followed by that of Example 6, Example 9 and Example 8 in that order.

TABLE 3

Control Absorption of KTM
Route of Administration: Intravenous
Administered Dose: 2 mg/kg
Plasma Concentration of KTM as ng/ml

| Sampling Time (hours) | Mean | ± S.D. |
|---|---|---|
| Basal | 0 | 0 |
| 0.083 | 14510 | 1999 |
| 0.25 | 7682 | 2887 |
| 0.5 | 3884 | 1891 |
| 1 | 1703 | 792 |
| 2 | 403 | 167 |
| 3 | 120 | 67 |
| 5 | 20 | 7 |

TABLE 4

Nasal Absorption of KTM
Composition: Example 1
Route of Administration: Intranasal
Administered Dose: 2 mg/kg/administration

| Sampling Time (hours) | Mean | ± S.D. |
|---|---|---|
| Basal | 18 | 16 |
| 0.25 | 2363 | 1035 |
| 0.5 | 1875 | 726 |
| 1 | 1103 | 490 |
| 2 | 593 | 217 |
| 3 | 267 | 55 |
| 5 | 121 | 52 |

TABLE 5

Nasal Absorption of KTM
Composition: Example 8
Route of Administration: Intranasal
Administered Dose: 2 mg/kg/administration

| Sampling Time (hours) | Mean | ± S.D. |
|---|---|---|
| Basal | 29 | 22 |
| 0.25 | 2973 | 1258 |
| 0.5 | 2654 | 880 |
| 1 | 2246 | 1145 |
| 2 | 1121 | 832 |
| 3 | 665 | 444 |
| 5 | 427 | 194 |

TABLE 6

Nasal Absorption of KTM
Composition: Example 9
Route of Administration: Intranasal
Administered Dose: 2 mg/kg/administration

| Sampling Time (hours) | Mean | ± S.D. |
|---|---|---|
| Basal | 35 | 17 |
| 0.25 | 2036 | 572 |
| 0.5 | 1663 | 778 |
| 1 | 1009 | 345 |
| 2 | 325 | 103 |
| 3 | 184 | 22 |
| 5 | 198 | 52 |

TABLE 7

Nasal Absorption of KTM
Composition: Example 6
Route of Administration: Intranasal
Dose Administered: 2 mg/kg/administration

| Sampling Time (hours) | Mean | ± S.D. |
|---|---|---|
| Basal | 23 | 20 |
| 0.25 | 1872 | 1228 |
| 0.5 | 1772 | 1027 |
| 1 | 1213 | 619 |
| 2 | 616 | 293 |
| 3 | 269 | 96 |
| 5 | 133 | 23 |

From the foregoing data, the following bioavailability parameters were calculated:

TABLE 8

| Formulation | i.v. | Example 1 (A) | Example 8 (B) | Example 9 (C) | Example 6 (D) |
|---|---|---|---|---|---|
| $AUC_{0-5}$ (h.ng/ml) | | | | | |
| average | 7355 | 3237 | 5972 | 2692 | 3197 |
| ± S.D. | 2405 | 1129 | 2973 | 571 | 976 |
| CV (%) | 32.7 | 34.9 | 49.8 | 21.2 | 30.5 |
| $T_{max}$ (hours) | | | | | |
| average | | 0.25 | 0.42 | 0.33 | 0.33 |
| ± S.D. | | 0 | 0.14 | 0.14 | 0.14 |
| CV (%) | | 0 | 34.6 | 43.3 | 43.3 |
| $C_{max}$ (ng/ml) | | | | | |
| average | | 2363 | 3226 | 2229 | 1895 |
| ± S.D. | | 1035 | 1079 | 335 | 1203 |
| CV (%) | | 43.8 | 33.4 | 15.0 | 63.5 |
| AUC i.n./AUC i.v. | | | | | |
| average | | 0.44 | 0.81 | 0.36 | 0.43 | i.n. = intranasal
i.v. = intravenous
Each value is the mean of the data obtained from three animals.

The foregoing results indicate that intranasal formulations of KETOROLAC® according to the invention compare favorably with intravenous formulations in terms of absorption (Formulation B from Example 8 being the best absorbed), time to maximum plasma concentration, and maximum plasma concentration and exhibit good absolute bioavailability (especially formulation B).

EXAMPLE 13

| Composition | % | For 10 Liters |
|---|---|---|
| KETOROLAC ® tromethamine | 15 | 1500 g |
| EDTA disodium | 0.01 | 1 g |
| NIPAGIN | 0.2 | 20 g |
| Purified water, q.s. to | 100 | 10 L |

Method of Preparation

In a suitable vessel equipped with mixer and heating sleeve, introduce about 9 liters of purified water and heat to a temperature of 80° C.

Dissolve NIPAGIN and EDTA disodium

Stir the solution constantly to complete dissolution of the components.

Cool the obtained solution to room temperature.

Dissolve KETOROLAC® tromethamine by stirring.

Bring to volume with water.

EXAMPLE 14

| Composition | % | For 10 Liters |
|---|---|---|
| KETOROLAC ® tromethamine | 15 | 1500 g |
| EDTA disodium | 0.01 | 1 g |
| NIPAGIN | 0.2 | 20 g |
| Glycocholic acid | 0.3 | 30 g |
| Purified water, q.s. to | 100 | 10 L |

Method of Preparation

In a suitable vessel equipped with mixer and heating sleeve, introduce about 9 liters of purified water and heat to a temperature of 80° C.

Dissolve NIPAGIN and EDTA disodium.

Stir the solution constantly to complete dissolution of the components.

Cool the obtained solution to room temperature.

Dissolve KETOROLAC® tromethamine and glycocholic acid by stirring.

Bring to volume with water.

EXAMPLE 15

| Composition | % | For 10 Liters |
|---|---|---|
| KETOROLAC ® tromethamine | 15 | 1500 g |
| EDTA disodium | 0.01 | 1 g |
| NIPAGIN | 0.2 | 20 g |
| Glycocholic acid | 0.3 | 30 g |
| Lutrol F 127 | 15 | 1500 g |
| Purified water, q.s. to | 100 | 10 L |

Method of Preparation

In a suitable vessel equipped with mixer and heating sleeve, introduce about 8 liters of purified water and heat to a temperature of 80° C.

Dissolve NIPAGIN and EDTA disodium.

Stir the solution to 4° C. and then, maintaining it between 4° and 6° C. throughout the operation, gradually add Lutrol F127 with stirring.

Continue stirring to complete hydration of the polymer.

Bring the solution to room temperature.

Dissolve KETOROLAC® tromethamine and glycocholic acid.

Bring to volume with water.

APPENDIX OF PRODUCT NAMES AND EXAMPLES OF COMMERCIAL SOURCES

KETOROLAC TROMETHAMINE: SYNTEX IRELAND, CLARECASTLE, IRELAND
HYDROXYPROPYLCELLULOSE (KLUCEL) DOW CHEMICAL CO, MIDLAND MI USA
HYDROXYPROPYLMETHYLCELLULOSE (METHOCEL) DOW CHEM. CO, MIDLAND MI
HYDROXYETHYLCELLULOSE (NATROSOL) HERCULES INC, WILMINGTON DE USA
SODIUM CARBOXYMETHYLCELLULOSE (BLANOSE) HERCULES INC, WILMINGTON DE
CARBOPOL: BF GOODRICH CHEMICAL CO., CLEVELAND, OH, USA
POLYCARBOPHIL: BF GOODRICH CHEMICAL CO., CLEVELAND, OH, USA
GUM TRAGACANTH: COLONY IP. & EXP. CO., NEW YORK, NY, USA
GUM XANTHAN: ALDRICH CHEMIE, STANHEIM, GERMANY
SODIUM ALGINATE: EDWARD MANDELL CO., CARMEL, NEW YORK, USA
AGAR AGAR: ALDRICH CHEMIE, STANHEIM, GERMANY
POLOXAMER (LUTROL f127): BASF WYNDOTTE CORP., PARSIPPANY, NJ, USA

ETHYL ALCOHOL: EASTMAN CHEMICAL PRODUCTS INC., KINOSPORT, TN, USA
ISOPROPYL ALCOHOL: BAKER CHEMICAL CO., NEW YORK, NY, USA
PROPYLENE GLYCOL: DOW CHEMICAL CO., MIDLAND, MI, USA
POLYETHYLENE GLYCOL: BASF WYNDOTTE CORP., PARSIPPANY, NJ, USA
DIISOPROPYLADIPATE: CRODA, GOOLE, NORTH HUMERSIDE, UK
SODIUM GLYCOCHOLATE: SIGMA CHEMICAL COMPANY, ST. LOUIS, MO, USA
LYSOPHOSPHATIDYLCHOLINE: AMERICAN LECITHIN, LONG ISLAND, NY, USA
METHYLPARAOXYBENZOATE (NIPAGIN): BDH CHEMICAL LTD, POOLE, DORSET, UK
PROPYLPARAOXYBENZOATE: BDH CHEMICAL LTD, POOLE, DORSET, UK
SODIUM BENZOATE: PFIZER INC., NEW YORK, NY, USA.
BENZYL ALCOHOL: BDH CHEMICAL LTD, POOLE DORSET, UK
BENZALCONIUM CHLORIDE: ION PHARMACEUTICALS, COVINA, CA, USA
CHLORBUTANOL: EASTERN CHEMICAL PRODUCTS, SMITHTOWN, NY USA
EDTA DISODIUM: GRACE AND CO., LONDON, UK.
POE(9)LAURYL ALCOHOL: BASF WYNDOTTE CORP, PARSIPPANY, NJ, USA
TROMETHAMINE: FARMITALIA, MILAN, ITALY
GLYCEROL: DOW CHEMICAL CO., MIDLAND, MI, USA
SODIUM CHLORIDE: ALDRICH CHEMIE, STANHEIM, GERMANY
GLUCOSE: ROQUETTE LTD, TUNBRIDGE WELLS, KENT, UK

What is claimed is:

1. An aqueous pharmaceutical formulation in the form of a nasal spray comprising an effective amount of an analgesic comprising ketorolac, an optical isomer thereof, or a salt thereof admixed with a bioadhesive polymer, wherein said spray when administered to a human subject intranasally generates plasma levels of ketorolac in the subject within the range of 0.3-5 mg/liter of plasma.

2. The pharmaceutical nasal spray of claim 1 wherein the analgesic is ketorolac tromethamine.

3. The nasal spray of claim 1 wherein the analgesic is present in the formulation in an amount of between 5 to 20% by weight based on total weight of the formulation.

4. The nasal spray of claim 3 wherein the analgesic is present in the formulation in an amount of 15% by weight based on total weight of the formulation.

5. The nasal spray of claim 1 wherein the bioadhesive polymer is selected from the group consisting of polyacrylics, cellulosics, and gums.

6. The nasal spray of claim 1, said spray being free of absorption enhancers.

7. A pharmaceutical formulation in the form of a nasal spray comprising an effective amount of an analgesic comprising ketorolac, an optical isomer thereof, or a salt thereof admixed with a bioadhesive polymer, wherein said spray when administered to a human subject intranasally forms a gel and generates plasma levels of ketorolac in the subject within the range of 0.3-5 mg/liter of plasma.

8. The nasal spray of claim 7 wherein the analgesic is ketorolac tromethamine.

9. The nasal spray of claim 7 wherein the analgesic is present in the formulation in an amount of between 5 to 20% by weight based on total weight of the formulation.

10. The nasal spray of claim 9 wherein the analgesic is present in the formulation in an amount of 15% by weight based on total weight of the formulation.

11. The nasal spray of claim 7 wherein the bioadhesive polymer is selected from the group consisting of polyacrylics, cellulosics, and gums.

12. The nasal spray of claim 7, said spray being free of absorption enhancers.

* * * * *